(12) United States Patent
Kim et al.

(10) Patent No.: US 6,525,318 B1
(45) Date of Patent: Feb. 25, 2003

(54) METHODS OF INSPECTING INTEGRATED CIRCUIT SUBSTRATES USING ELECTRON BEAMS

(75) Inventors: Yang hyong Kim, Seoul (KR);
Hyo-cheon Kang, Kyungki-do (KR);
Deok-yong Kim, Kyungki-do (KR);
Sang-myun Lee, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 09/384,885

(22) Filed: Aug. 27, 1999

(30) Foreign Application Priority Data

Apr. 23, 1999 (KR) .............................. 99-14626

(51) Int. Cl.$^7$ .............................................. H01J 37/256
(52) U.S. Cl. ...................................... 250/310; 250/307
(58) Field of Search ................................. 250/310, 306, 250/307; 324/501, 537, 158 R (56) References Cited

U.S. PATENT DOCUMENTS

| | | | |
|---|---|---|---|
| 4,326,165 A | 4/1982 | Szedon .................... | 324/158 R |
| 4,985,681 A | 1/1991 | Brunner et al. .............. | 324/501 |
| 5,023,453 A | 6/1991 | Adachi et al. ............... | 250/309 |
| 5,057,689 A | 10/1991 | Nomura et al. .............. | 250/310 |
| 5,302,828 A | 4/1994 | Monahan .................... | 250/307 |
| 5,493,116 A | 2/1996 | Toro-Lira et al. ........... | 250/310 |
| 5,773,989 A | 6/1998 | Edelman et al. ............. | 324/765 |
| 5,825,035 A | 10/1998 | Mizumura et al. ....... | 250/423 R |
| 5,877,498 A | * 3/1999 | Sugimoto et al. ........... | 250/310 |
| 5,986,263 A | 11/1999 | Hiroi et al. ................. | 250/310 |
| 6,067,153 A | 5/2000 | Mizuno ....................... | 356/237 |

FOREIGN PATENT DOCUMENTS

EP    0 504 944 A2    9/1992

OTHER PUBLICATIONS

Notice to Submit Response (and Translation), Mar. 29, 2001, Korean Application No. 1999–14626.

* cited by examiner

*Primary Examiner*—Kiet T. Nguyen
(74) *Attorney, Agent, or Firm*—Myers Bigel Sibley & Sajovec (57) ABSTRACT

Methods of inspecting integrated circuit substrates include the steps of directing a beam of electrons into a first conductive plug located within a first contact hole on an integrated circuit substrate and then measuring a quantity of electrons emitted from the first conductive plug to determine an absence or presence of an electrically insulating residue in the first contact hole. The quantity of electrons emitted from the first conductive plug by secondary electron emission can be measured in order to determine whether electrons are being accumulated within the conductive plug because an insulating residue is blocking passage of the electrons into an underlying conductive portion of the substrate. If an electrically insulating residue is present, then sufficient repulsive forces between the accumulated electrons will result in the secondary emission of excess electrons from an upper surface of the conductive plug as the conductive plug is being irradiated with the electron beam. A detector can then be used to measure the quantity of the emitted electrons against a threshold level, in order determine whether the quantity of electrons emitted by secondary emission is sufficient to indicate that an insulating residue is present in the contact hole.

20 Claims, 12 Drawing Sheets

METHODS OF INSPECTING INTEGRATED CIRCUIT SUBSTRATES USING ELECTRON BEAMS

FIELD OF THE INVENTION

The present invention relates to methods of inspecting integrated circuit substrate, and more particularly to methods of inspecting integrated circuit substrates at intermediate stages of fabrication.

BACKGROUND OF THE INVENTION

As a design rule gets smaller in fabricating semiconductor devices, it becomes very difficult to form a contact hole which opens a predetermined portion of a semiconductor substrate. Accordingly, it is important to monitor whether or not a contact hole is formed properly on a semiconductor substrate. In particular, by effectively monitoring in-line the state, open or not-open, of a contact hole during fabrication of a semiconductor device, the time required for fabricating the semiconductor device can be reduced and the yield can be greatly enhanced.

However, conventional in-line monitoring of an open or not-open state of a contact hole has been performed manually by an operator using a general image measurement apparatus. In this case, a monitoring error may result from the manual operation and thus unreliable results may be obtained.

Also, in order to monitor the open or not-open state of a contact hole using the general image measurement apparatus, a high voltage of about 20 KV must be used. However, if a high voltage such as about 20 KV is used, it is not possible to precisely monitor the state, open or not-open, of a contact hole.

Figure 1:
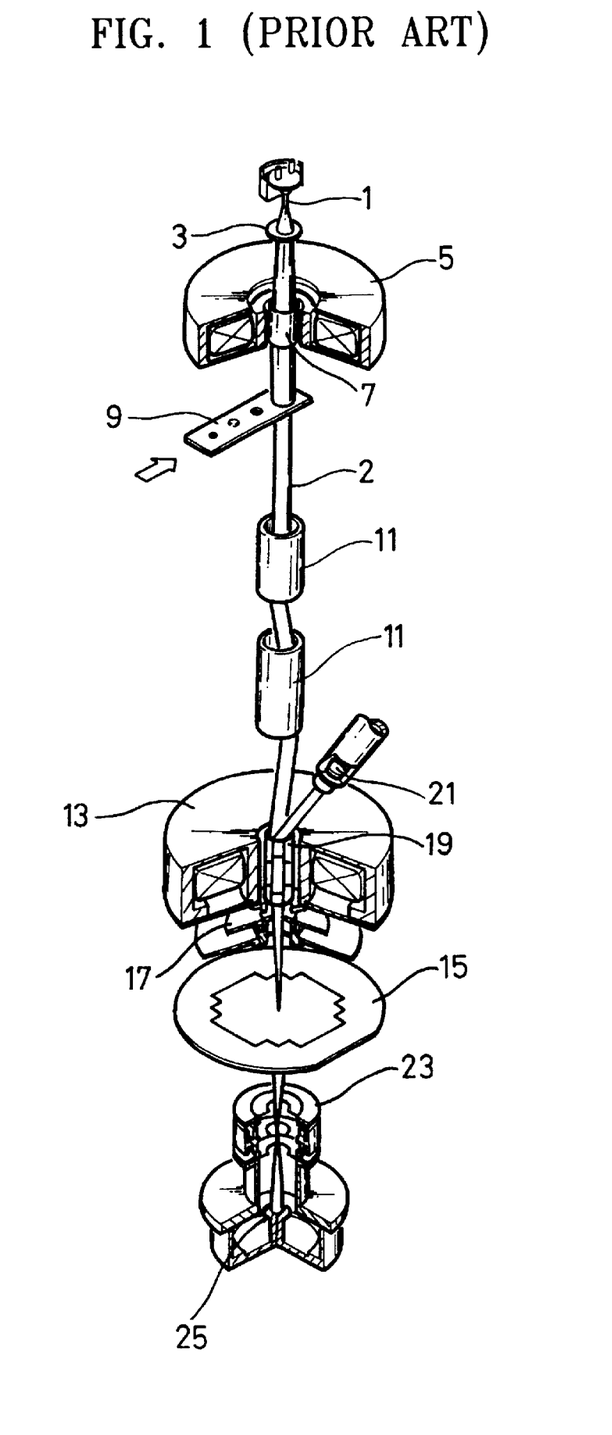
FIG. 1 is a perspective view of an electron beam inspection apparatus according to the prior art.
Figure 2:
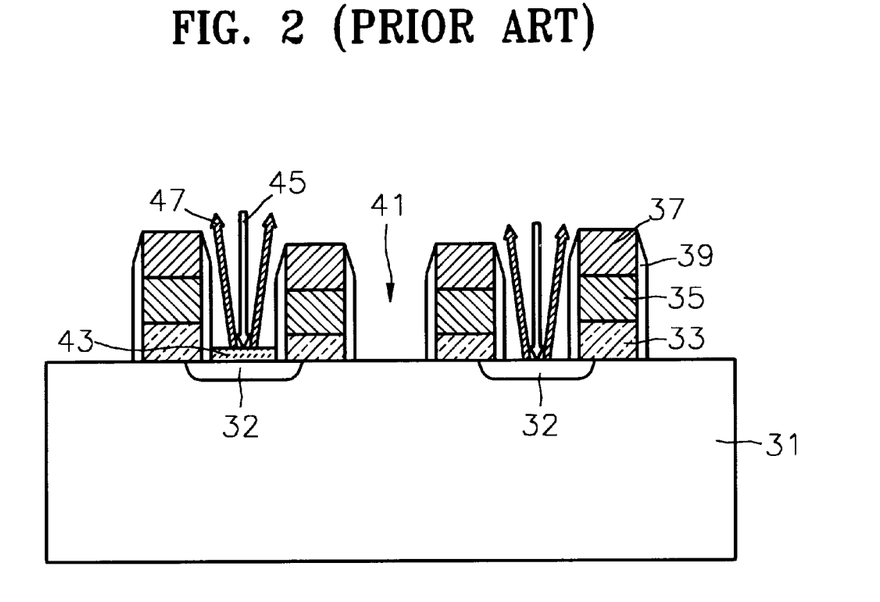
FIG. 2 is a cross-sectional view of an integrated circuit substrate undergoing inspection by an electron beam, according to the prior art.

FIG. 1 is a schematic diagram illustrating a conventional electron beam inspection apparatus, and FIG. 2 illustrates a semiconductor substrate used for determining whether a contact hole is in an open or not-open state. In detail, the electron beam inspection apparatus shown in FIG. 1 includes an electron-beam gun 1 for supplying electron beams. The electron beams are emitted from the electron-beam gun 1 and are accelerated before passing through a gun aperture 3. The electron beam inspection apparatus includes electron beam receiving means which allows an electron beam to move properly toward a sample, e.g., the surface of a semiconductor substrate, for scanning the semiconductor substrate. Here, a condenser lens 5 collimates the diverging electron beam 2 and the collimated electron beam 2 passes through an electrostatic octapole 7 for astigmatism correction and alignment. Then, the electron beam 2 having passed through the electrostatic octapole 7 passes through a beam adjusting aperture 9 and an icosapole deflector 11. The electron beam 2 having passed through the beam adjusting aperture 9 and the icosapole deflector 11 passes through an objective lens 13 to then be incident on a sample 15 shown in FIG. 2. Either a positive voltage or a negative voltage may be applied to the sample 15 in the electron beam inspection apparatus. An x-y stage (not shown) capable of moving in x and y axes directions and supporting the sample 15 is provided under the sample 15.

In the electron beam inspection apparatus, secondary electrons emitted from the sample 15 after passing through the objective lens 13 are detected by a secondary electron detector 21 via an extraction electrode 17 and a Wien filter 19. A positive voltage is applied to the extraction electrode 17 and a negative voltage is applied to the sample 15 so that the secondary electrons move to the secondary electron detector 21 via the Wien filter 19 to then be detected. The Wien filter 19 comprised of an electrostatic octapole and a 60° magnetic field deflector, removes opposed electric and magnetic deflections for the electron beam 2. The sample 15 may be in the form of a semiconductor substrate 31 shown in FIG. 2, or a mask substrate (not shown). If the sample 15 is a mask substrate having an electron beam transmission area, the electron beam 2 is received by a transmitted electron detector 25 via an electrostatic transmission lens 23 to then be detected.

The possibility of determining in-line the state, open or not-open, of a contact hole will now be evaluated in the case of testing the sample semiconductor substrate shown in FIG. 2 with the electron beam inspection apparatus shown in FIG. 1. First, the sample semiconductor substrate shown in FIG. 2 tested with the electron beam inspection apparatus shown in FIG. 1 will be described. In detail, a gate oxide layer (not shown), a gate electrode consisting of a polysilicon layer 33 and a tungsten silicide layer 35, and an insulation layer 37 for insulating the gate electrode are sequentially formed on a p-type silicon substrate 31 having an n-type impurity region 32 to be a source and a drain. Spacers 39 are formed at both side walls of the stacked structure of the gate electrode and the insulation layer 37. A contact hole 41 which exposes the silicon substrate 31 between the spacers 39 is formed. Next, in-line monitoring of whether a contact hole formed in the semiconductor substrate shown in FIG. 2 is in an open or not-open state is performed using the electron beam inspection apparatus shown in FIG. 1. Here, if an unetched material layer 43 shown in FIG. 2 (e.g., an oxide or nitride layer) is present in the contact hole, primary electrons (represented by reference numeral 45 in FIG. 2) do not flow properly to the silicon substrate 31 so that electrons accumulate on the surface of the unetched material layer 43. Then, a large amount of secondary electrons (represented by reference numeral 47 in FIG. 2) are emitted from the surface of the silicon substrate 31 due to repulsive force of electrons. Depending on a difference in secondary electron yields, a brighter (white) or darker (black) image is displayed for a portion where a large amount of secondary electrons 47 are emitted, that is, a portion where the unetched material layer 43 is present, compared to portions where the unetched material layer 43 is not present.

Figure 3:
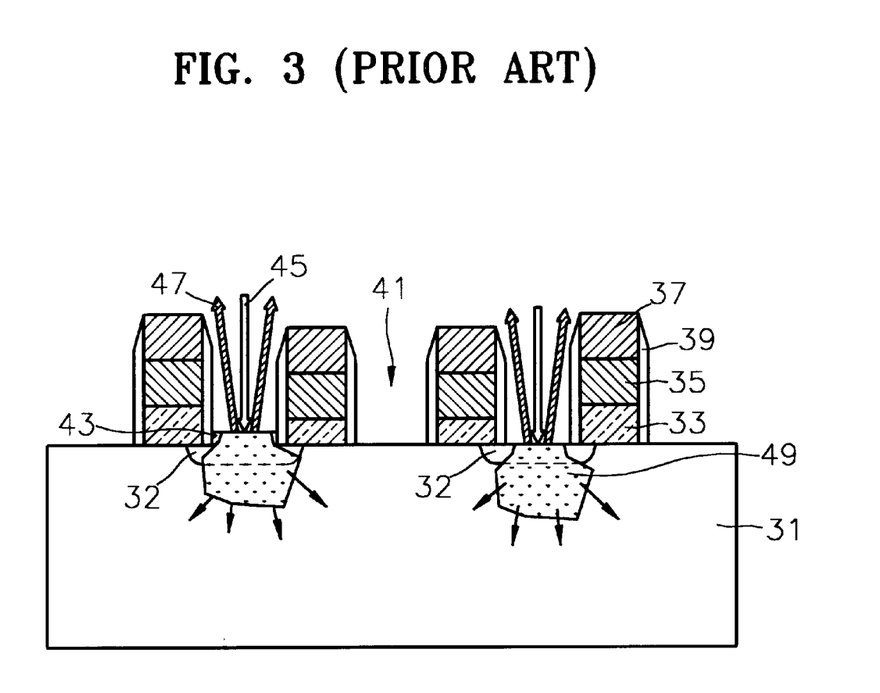
FIG. 3 is another cross-sectional view of an integrated circuit substrate undergoing inspection by an electron beam, according to the prior art.

Notwithstanding this method of performing in-line inspection, it may still be difficult to reliably detect the presence of unetched material. For example, FIG. 3 illustrates movement of primary and secondary electrons when performing in-line monitoring of a contact hole using the electron beam inspection apparatus shown in FIG. 1. In FIG. 3, the same reference numerals as those of FIG. 2 denote the same elements. In detail, the primary electrons 45 incident on the substrate 31 are activated within the unetched material layer 43 in the contact hole and in the substrate 31 and then move toward the lower portion of the substrate 31. Then, since the difference in secondary electron yields between a portion with the unetched material layer 43 and a neighboring portion without the unetched material layer 43 is not large, the bright and dark sections of the image are not as distinguishable. Thus, it may be difficult to inspect the state, open or not-open, of the contact holes shown in FIGS. 2 and 3, by using the electron beam inspection apparatus shown in FIG. 1.

Figure 4A:
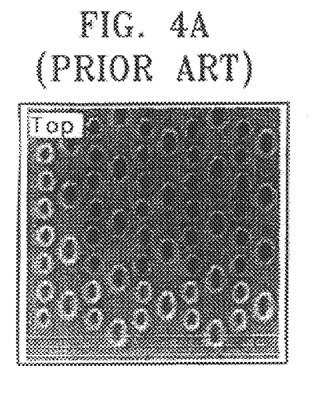
FIGS. 4A–4C, 5A–5C and 6A–6C illustrate images generated upon inspection of an integrated circuit substrate containing oxide residues in contact holes therein, using the apparatus of FIG. 1.
Figure 4B:
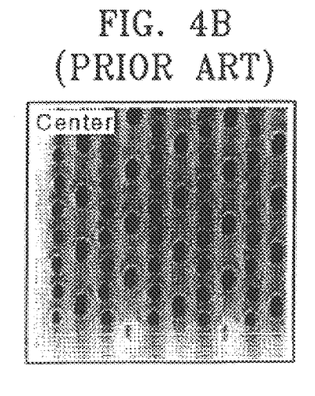
Figure 4C:
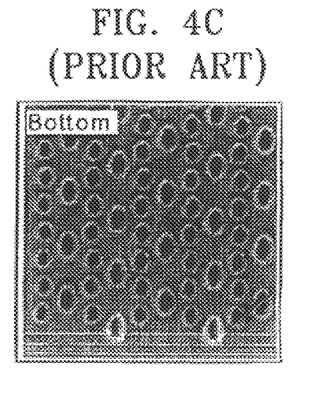
Figure 5A:
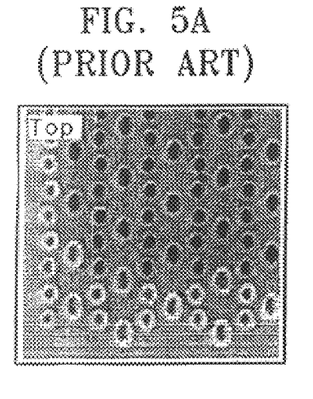
Figure 5B:
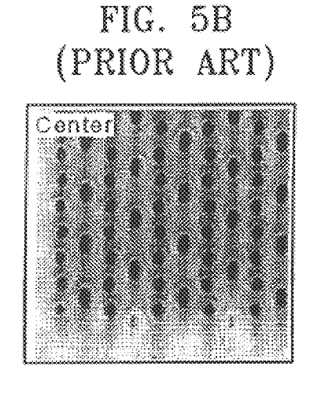
Figure 5C:
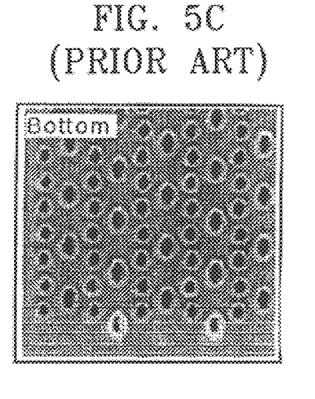
Figure 6A:
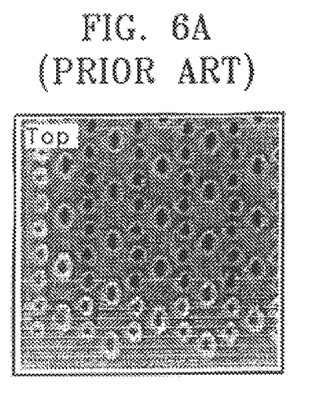
Figure 6B:
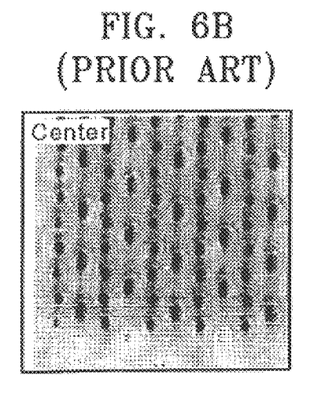
Figure 6C:
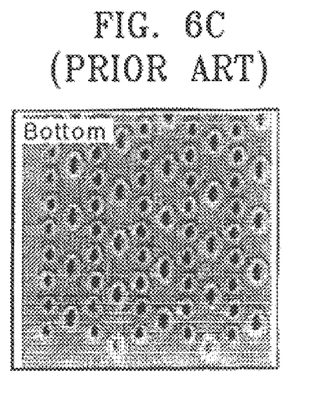

FIGS. 4 through 6 illustrate images of contact holes observed by a high-voltage electron beam inspection apparatus in the case when the unetched material layer shown in FIG. 3 is an oxide layer. In detail, FIGS. 4A through 4C show that the unetched material layer 43 shown in FIG. 3 (i.e., an oxide layer) is removed by etching. Specifically, in view of a flat zone of a semiconductor wafer, FIG. 4A shows a cell portion present on the top of the semiconductor wafer, FIG. 4B shows a cell portion in the center thereof, and FIG. 4C shows a cell portion at the bottom thereof. In these cases, the oxide layer on the edge portion of the cell is not completely etched, thus preventing the contact hole from being opened, so that a bright image is displayed. The oxide layer of the interior portion of the cell is completely etched, so that a dark image is displayed. FIGS. 5A through 5C show cases where the thickness of the unetched material layer 43 is 300 Å. Here, like in FIGS. 4A through 4C, in view of a flat zone of a semiconductor wafer, FIG. 5A shows a cell portion on the top of the semiconductor wafer, FIG. 5B shows a cell portion in the center thereof, and FIG. 5C shows a cell portion at the bottom thereof. In these cases, a bright image is displayed on the edge portion of the cell, and a dark image is displayed on the interior portion of the cell. Even if the thicknesses of the oxide layers shown in FIGS. 5A through 5C are set to 300 Å, the oxide layers shown in FIGS. 5A through 5C are not discernible from those shown in FIGS. 4A through 4C. Thus, the state (open or not-open) of a contact hole cannot be determined. FIGS. 6A through 6C show cases where the thickness of the unetched material layer 43 shown in FIG. 3 is 500 Å. Similarly, in view of a flat zone of a semiconductor wafer, FIG. 6A indicates a cell portion on the top of the semiconductor wafer, FIG. 6B indicates a cell portion in the center thereof, and FIG. 6C indicates a cell portion at the bottom thereof. In these cases, a bright image is displayed on the edge portion of the cell, and a bright image is displayed on the rim of a contact hole in the interior portion of the cell, which suggests that the contact hole is not opened. Therefore, if the thickness of the unetched material layer 43 as the oxide layer is set to 500 Å, it can be determined whether a contact hole is in an open or not-open state. Thus, in order to reliably inspect the state of a contact hole using the electron beam inspection apparatus shown in FIG. 1, the thickness of the unetched oxide material layer 43 must be at least 500 Å.

Figure 7A:
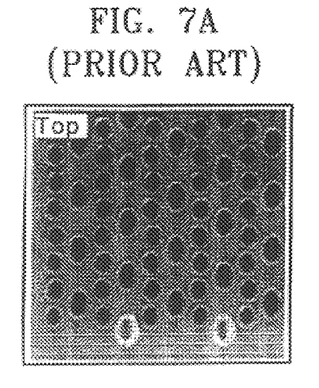
FIGS. 7A–7C and 8A–8C illustrate images generated upon inspection of an integrated circuit substrate containing nitride residues in contact holes therein, using the apparatus of FIG. 1.
Figure 7B:
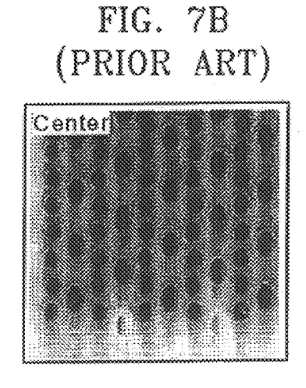
Figure 7C:
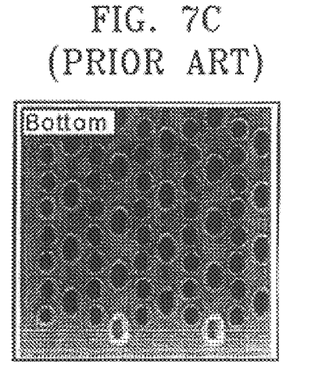

FIGS. 7 and 8 illustrate images of contact holes observed by a high-voltage electron beam inspection apparatus in the case when the unetched material layer shown in FIG. 3 is a nitride layer. In detail, FIGS. 7A through 7C show images of contact holes observed by a high-voltage electron beam inspection apparatus in the case where the unetched material layer shown in FIG. 3 is a nitride layer. Here, in view of a flat zone of a semiconductor wafer, FIG. 7A indicates a cell portion on the top of the semiconductor wafer, FIG. 7B indicates a cell portion in the center thereof, and FIG. 7C indicates a cell portion at the bottom thereof. In these cases, the nitride layer is not completely etched at the edge portion of the cell, so that the contact hole is not opened, thereby causing a bright image to be displayed. In the interior portion of the cell, the nitride layer is completely etched, thereby displaying a dark image.

Figure 8A:
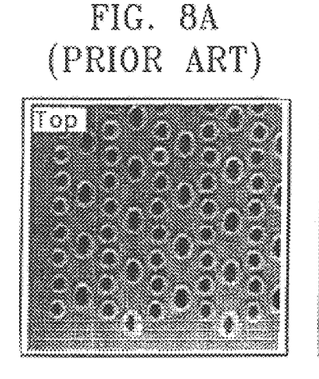
Figure 8B:
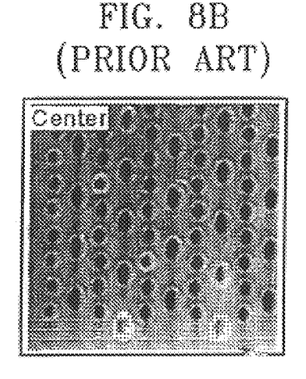
Figure 8C:
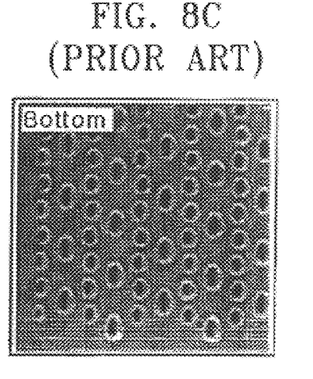

FIGS. 8A through 8C show images of contact holes observed by a high-voltage electron beam inspection apparatus in the case where the unetched nitride material layer 43 is 300 Å thick. Here, in view of a flat zone of a semiconductor wafer, FIG. 8A indicates a cell portion on the top of the semiconductor wafer, FIG. 8B indicates a cell portion in the center thereof, and FIG. 8C indicates a cell portion at the bottom thereof. In these cases, a bright image is displayed at the edge portion of the cell, and a dark image is displayed in the interior portion of the cell. That is to say, the contact hole is in a "not-open" state. Therefore, it can be determined whether a contact hole is in an open or not-open state when the thickness of the nitride layer is set to 300 Å.

Notwithstanding the ability to reliably detect the presence of unetched material in contact holes when that material is of sufficient thickness (at least 500 Å for oxide and at least 300 Å for nitride), there continues to be a need to more reliably detect the presence of unetched material in contact holes when the unetched material is thinner than 300 Å.

SUMMARY OF THE INVENTION

It is therefore an object of the present invention to provide improved methods of inspecting integrated circuit substrates.

It is another object of the present invention to provide methods of detecting the presence of insulating residues in contact holes on integrated circuit substrates.

These and other objects, advantages and features of the present invention are provided by methods of inspecting integrated circuit substrates (e.g. wafers) to determine whether unwanted insulating residues remain in contact holes thereon, after etching or related fabrication steps have been performed. These integrated circuit substrate inspection methods preferably include the steps of directing a beam of electrons into a first conductive plug located within a first contact hole on an integrated circuit substrate and then measuring a quantity of electrons emitted from the first conductive plug to determine an absence or presence of an electrically insulating residue in the first contact hole. In particular, the quantity of electrons emitted from the first conductive plug by secondary electron emission can be measured in order to determine whether electrons are being accumulated within the conductive plug because an insulating residue is blocking passage of the electrons into an underlying conductive portion of the substrate. If an electrically insulating residue is present, then sufficient repulsive forces between the accumulated electrons will result in the secondary emission of excess electrons from an upper surface of the conductive plug as the conductive plug is being irradiated with the electron beam. A detector can then be used to measure the quantity of the emitted electrons against a threshold level, in order to determine whether the quantity of electrons emitted by secondary emission is sufficient to indicate that an insulating residue is present in the contact hole.

The reliability of these methods to determine whether insulating residues remain within contact holes after etching can also be increased by annealing the integrated circuit substrate and etching back the electrically insulating layer in which the contact holes are formed to more fully expose the conductive plugs within the contact holes. This etching step preferably comprises the step of exposing the electrically insulating layer and the conductive plugs therein to an etching solution comprising HF and $NH_4OH$. The annealing step may also comprise the step of annealing the integrated circuit substrate at a temperature greater than about 800° C. for a duration greater than about one (1) hour. In order to increase the rate at which electrons within the electron beam are transferred from the conductive plugs into the conductive portion of the substrate, a voltage of greater than 100 volts is preferably applied across the semiconductor wafer.

According to another embodiment of the present invention, a method of inspecting an integrated circuit substrate having upper and lower electrically insulating layers stacked thereon may include the steps of directing a beam of electrons into a first conductive plug located within a first contact hole in the upper electrically insulating layer and measuring a quantity of electrons emitted from the first conductive plug to determine an absence or presence of an electrically insulating residue in a second contact hole in the lower electrically insulating layer. Thus, even during back-end processing after multiple insulating layers have been formed on an integrated circuit substrate, the methods of the present invention can be utilized to detect the presence of insulating residues formed in contact holes of underlying insulating layers.

DESCRIPTION OF PREFERRED EMBODIMENTS

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 9:
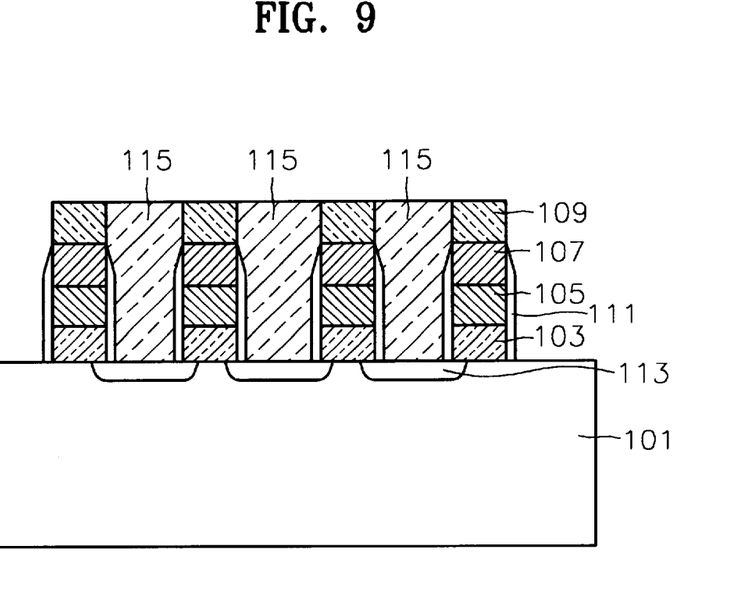
FIG. 9 is a cross-sectional view of an integrated circuit substrate that can be inspected in accordance with a first embodiment of the present invention.
Figure 10:
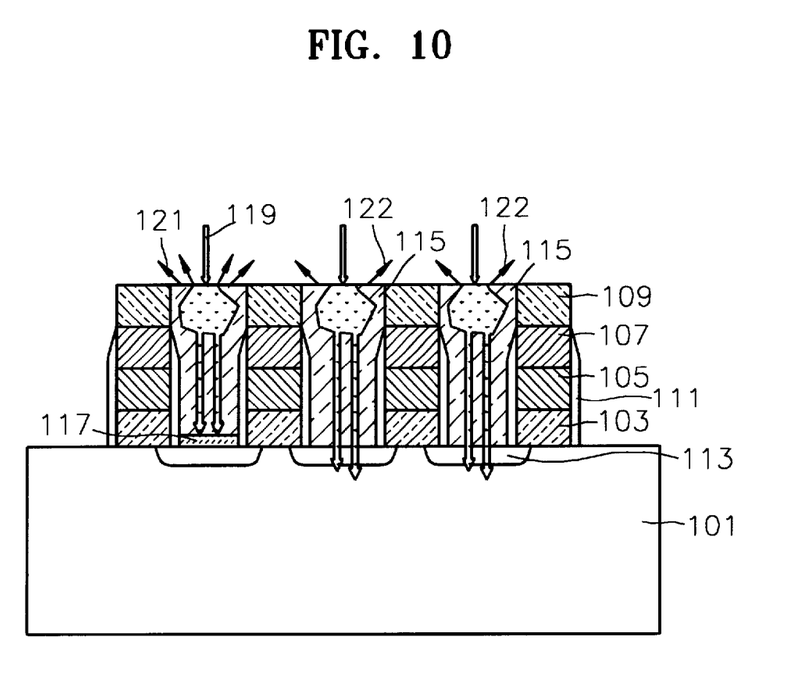
FIG. 10 is a cross-sectional view of the substrate of FIG. 9 undergoing an inspection method according to an embodiment of the present invention.
Figure 11:
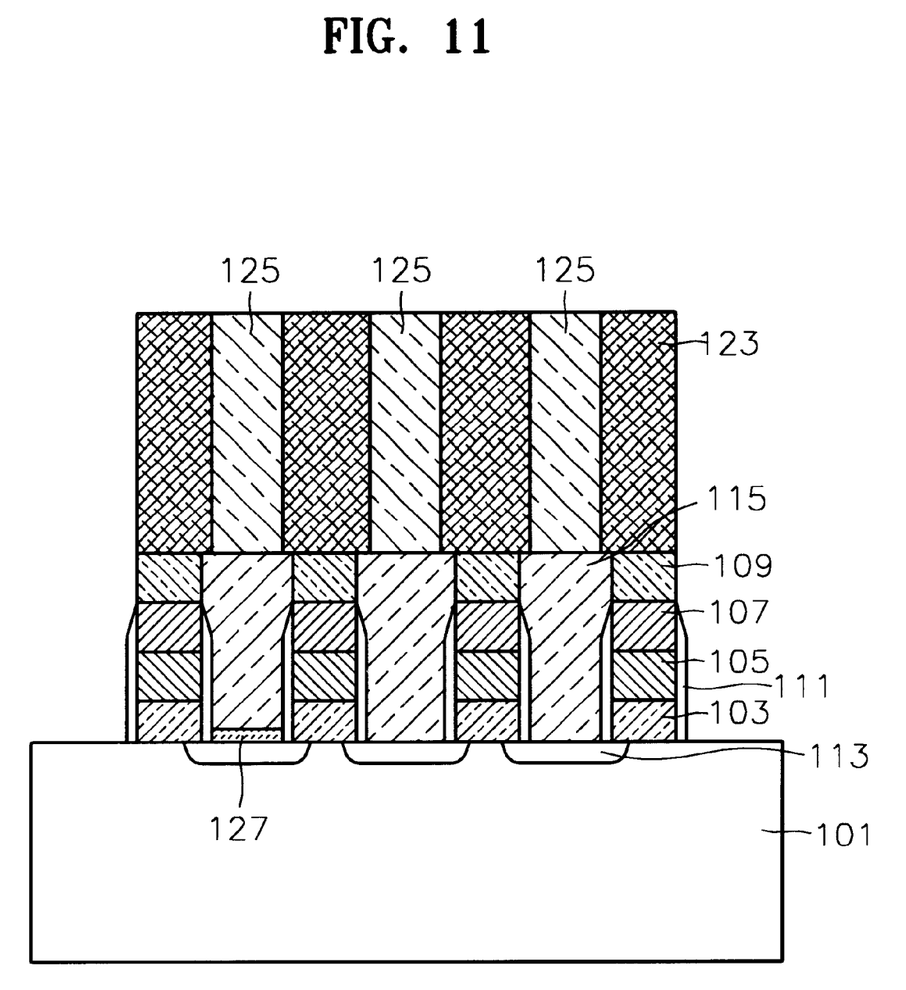
FIG. 11 is a cross-sectional view of an integrated circuit substrate that can be inspected in accordance with a second embodiment of the present invention.

Referring now to FIGS. 9–11, preferred methods of inspecting integrated circuit substrates (e.g. wafers) to determine whether unwanted insulating residues remain in contact holes thereon will be described. As illustrated by FIG. 9, an integrated circuit substrate may be formed by defining a plurality of insulated electrodes (e.g., insulated gate electrodes) on a semiconductor substrate 101. These insulated electrodes may be defined by initially forming a composite layer that includes a gate oxide layer (not shown), a polysilicon layer 103, a tungsten silicide layer 105 and an insulating layer 107 and then using an etching mask to pattern the composite layer as a plurality of electrodes. Sidewall insulating spacers 111 may also be formed on sidewalls of the insulated gate electrodes, as illustrated. Dopant implantation and diffusion techniques may then be used to define a plurality of impurity regions 113 in the substrate 101. As will be understood by those skilled in the art, these impurity regions 113 may be formed in a self-aligned manner to the insulated electrodes. An electrically insulating layer 109 (e.g., $SiO_2$ layer) may then be formed on the insulated electrodes and on the impurity regions 113. Conventional photolithographically defined etching steps may then be performed to define a plurality of contact holes in the electrically insulating layer 109. These contact holes preferably expose the face of the substrate 101 and the impurity regions 113 therein. However, electrically insulating residues may remain at the bottoms of some holes in the event the etching step is not performed satisfactorily. The presence of insulating residues is particularly prevalent when contact holes having high aspect ratios are defined. A blanket layer of a conductive material (e.g., doped-polysilicon, W, Al, Cu) can then be conformally deposited on the insulating layer 109 and in the contact holes. Next, planarization and/or etch-back steps can be performed on the blanket layer to define a plurality of conductive plugs 115 (e.g., polysilicon plugs) in the contact holes.

Steps are then performed to inspect the integrated circuit substrate at an intermediate stage of processing to determine whether any electrically insulating residues 117 remain in the contact holes. In contrast to the prior art method described with respect to FIGS. 2–3, these inspection steps are performed by an electron beam apparatus after the contact holes are filled with electrically conductive contact plugs 115. In particular, the preferred inspection method includes the steps of directing a beam 119 of electrons into a first conductive plug 115 and then measuring a quantity of electrons 121 emitted from the first conductive plug to determine an absence or presence of an electrically insulating residue 117 in the corresponding contact hole. The quantity of electrons 121 emitted from the first conductive plug (by secondary electron emission) is then measured to determine whether electrons are being accumulated within the conductive plug 115 because an insulating residue 117 is blocking passage of the electrons into an underlying conductive portion of the substrate 101. If an electrically insulating residue 117 is present, then sufficient repulsive forces between the accumulated electrons will result in the secondary emission of excess electrons 121 at a relatively high level from an upper surface of the conductive plug 115 as the conductive plug 115 is being irradiated with the electron beam 119. If an electrically insulating residue 117 is not present, then many of the electrons within the beam 119 will be transferred into the substrate.

A detector, such as the detector 21 illustrated in FIG. 1., can be used to measure and compare the quantity of the emitted electrons 121 against a threshold or other reference level. For example, if the quantity of electrons 121 emitted by secondary emission from a conductive plug 115 is sufficiently greater than the quantity of electrons 122 emitted from another (e.g., adjacent) conductive plug 115 that can be used as a reference (e.g., because it is free of any residue), then the detector (and supporting hardware and software) will "flag" the corresponding contact hole as being defective. In the event one or more defective contact holes are detected, then conventional techniques can be used to remove the conductive plugs 115 and then remove any remaining residues 117 from the contact holes by performing additional etching and residue cleaning steps.

The reliability of these inspection methods to determine whether insulating residues remain within contact holes after etching can also be increased by annealing the integrated circuit substrate and etching back the electrically insulating layer in which the contact holes are formed to more fully expose the upper surfaces of the conductive plugs within the contact holes. As determined by the inventors herein, steps to increase the exposed surface area of the conductive plugs will result in greater secondary electron emission when an insulating residue is present and lead to greater secondary electron detection efficiency. This etching step preferably comprises the step of exposing the electrically insulating layer and the conductive plugs therein to an etching solution comprising HF and $NH_4OH$. The annealing step may also comprise the step of annealing the integrated circuit substrate at a temperature greater than about 800° C. for a duration greater than about one (1) hour. Moreover, in order to increase the rate at which electrons within the electron beam are transferred from the conductive plugs into the conductive portion of the substrate in the event a residue is not present, a voltage of greater than 100 volts is preferably applied across the semiconductor wafer to attract the primary electrons from the electron beam 119 into the substrate. In addition, by accounting for a reversal in the relative magnitudes of secondary electron emission from the portion of the electrically insulating layer surrounding a conductive plug and the magnitude of secondary electron emission from the conductive plug, substrate voltages of greater than 800 volts may also be used, as explained more fully hereinbelow with respect to FIG. 12.

According to another embodiment of the present invention, the measurement of secondary electron emission from conductive plugs in upper contact holes can also be used to determine the presence or absence of electrically insulating residues in lower or underlying contact holes. For example, as best illustrated by FIG. 11, the structure of FIG. 9 may be modified by patterning a second electrically insulating layer 123 on the first electrically insulating layer 109 and then forming a plurality of second conductive plugs 125 in the second electrically insulating layer 123. The second conductive plugs 125 may comprise the same material as the first conductive plugs 115. As illustrated, these second conductive plugs 125 align and form ohmic contacts to respective ones of the underlying first conductive plugs 115. Based on this embodiment, the above-described steps may be performed to inspect the integrated circuit substrate by directing a beam of electrons into an upper conductive plug 125 located within an upper contact hole in the upper electrically insulating layer and then measuring a quantity of electrons emitted from the upper conductive plug 125 to determine an absence or presence of an electrically insulating residue 127 in a lower contact hole in the lower electrically insulating layer 109. Accordingly, even during back-end processing after multiple insulating layers have been formed on an integrated circuit substrate, the methods of the present invention can be utilized to detect the presence of insulating residues formed in contact holes of underlying insulating layers.

In addition to the secondary emission of electrons from the upper surfaces of conductive plugs formed in holes blocked by insulating residues, secondary emission of electrons will also take place from those adjacent portions of the insulating layer that surround the conductive plug. Accordingly, the software and/or hardware used to control the inspection tool should take into account differences in the secondary electron yields from a conductive plug ($SE_{Si}$) and the insulating regions ($SE_{Ox}$) that surround the conductive plug. As will be understood by those skilled in the art, the secondary electron yields from silicon and silicon dioxide can be determined using the following equations:

$$SE_{Si} = 1.34245(1 + 0.0397887a^2) \left[ \frac{E^{1-\frac{2.21828}{-0.5+300(1+0.477465a^2)}}}{-0.5 + 300(1 + 0.477475a^2)} \right]^{0.25} \quad (1)$$

$$SE_{ox} = 3.44151(1 + 0.098676a^2) \left[ \frac{E^{1-\frac{2.21828}{-0.5+300(1+0.477465a^2)}}}{-0.5 + 300(1 + 0.477465a^2)} \right]^{0.62} \quad (2)$$

where "a" is the incidence angle of an electron beam (in radians), and E is the electron beam energy (eV).

Figure 12:
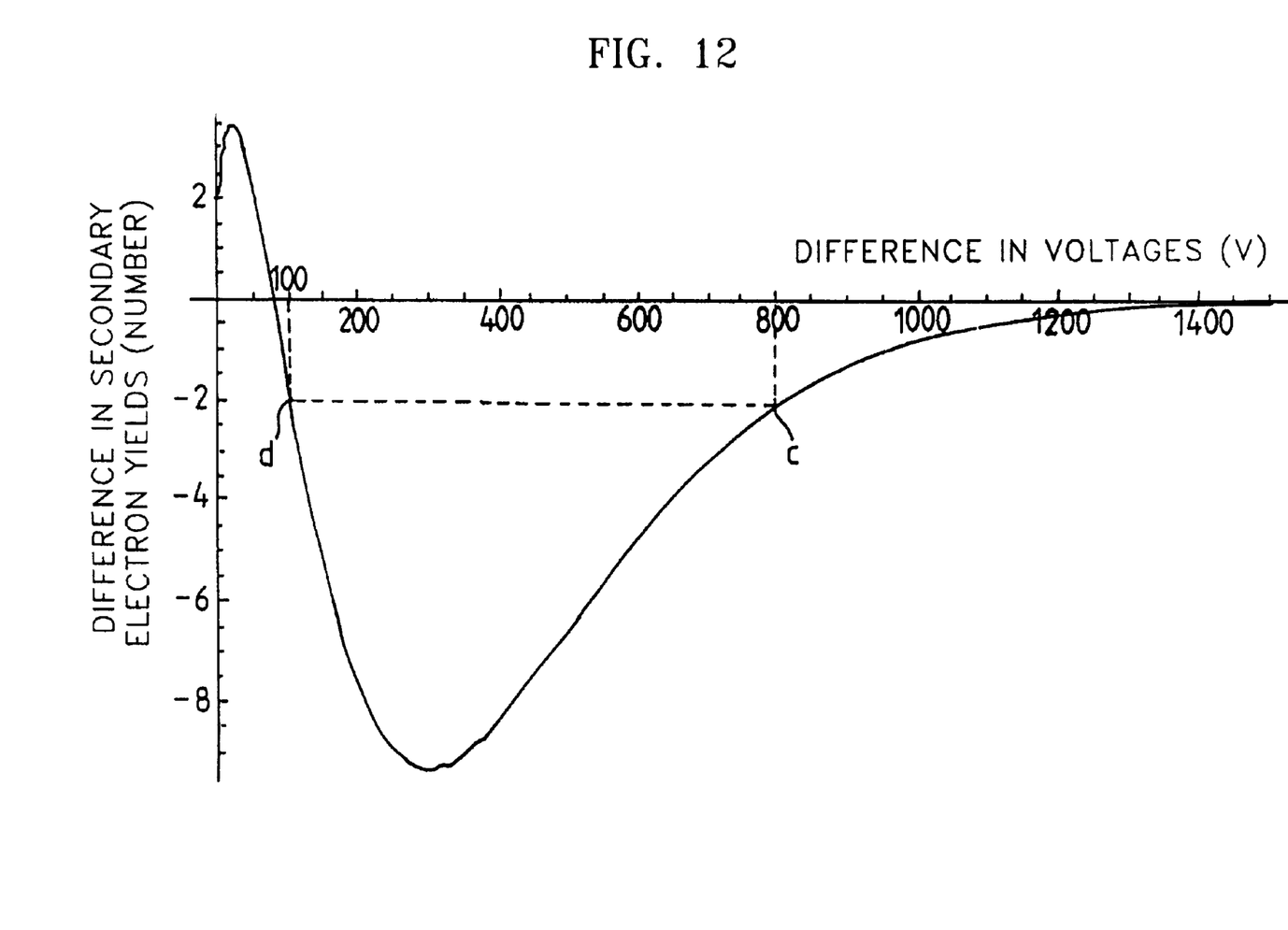
FIG. 12 is a graph of substrate bias (y-axis) versus difference in secondary electron yields (x-axis) according to the present invention.

As determined by the inventors herein, the magnitude of the voltage applied across the semiconductor substrate 101 (e.g., wafer) can be adjusted to a preferred level that maximizes the degree of secondary electron yield difference. This increases the likelihood of accurately detecting the presence of insulating residues even if the residues are relatively thin or do not completely block a respective contact hole. In other words, by increasing the yield difference between ($SE_{Si}$) and ($SE_{Ox}$), the likelihood that measurements of the secondary electron emission from a respective conductive plug will be obscured by very high or very low levels of secondary emission from adjacent insulating regions can be decreased. This aspect of the present invention is best illustrated by FIG. 12 which represents a graph of substrate voltage versus difference in secondary electron yields ($SE_{Si}$–$SE_{Ox}$). Based on this graph, a substrate voltage in a range between 100 and 800 volts will result in a relatively high difference in yield. This preferred range is further identified by points "c" and "d" which graphically illustrate the highest substrate voltage that can be applied for reliable results and the lowest substrate voltage that can be applied for reliable results. Furthermore, the difference between the secondary electron yields of oxide and silicon makes it possible to monitor the "open" or "closed" state of a contact hole because a greater difference in secondary electron yields of oxide and silicon makes the detection of a voltage difference between adjacent conductive pads of the semiconductor substrate more reliable. In particular, when the voltage difference between the top and bottom surfaces of the semiconductor substrate is 400 volts, the difference in secondary electron yields between the adjacent conductive pads can be readily detected.

Various experiments in a high-voltage area, in which the voltage difference between top and bottom surfaces of a semiconductor substrate was in the range of 800–1500 volts, were performed. The experimental results showed that the voltage difference between adjacent conductive pads could be increased by annealing the substrates of FIGS. 9 and 11 at a temperature greater than about 800° C. for a duration greater than about one hour, and more preferably at 850° C. for a duration of two (2) hours. Improvements in detection reliability were also noticed when the substrates of FIGS. 9 and 11 were etched using a mixed solution of HF, $NH_4OH$ and pure water. The sequence of the annealing and etching steps can also be reversed. Accordingly, notwithstanding the suggestion by FIG. 12 that high voltages of greater than 800 volts may not be preferred, high voltages may be used, particularly if the above-described annealing and etching steps are performed.

Figure 13:
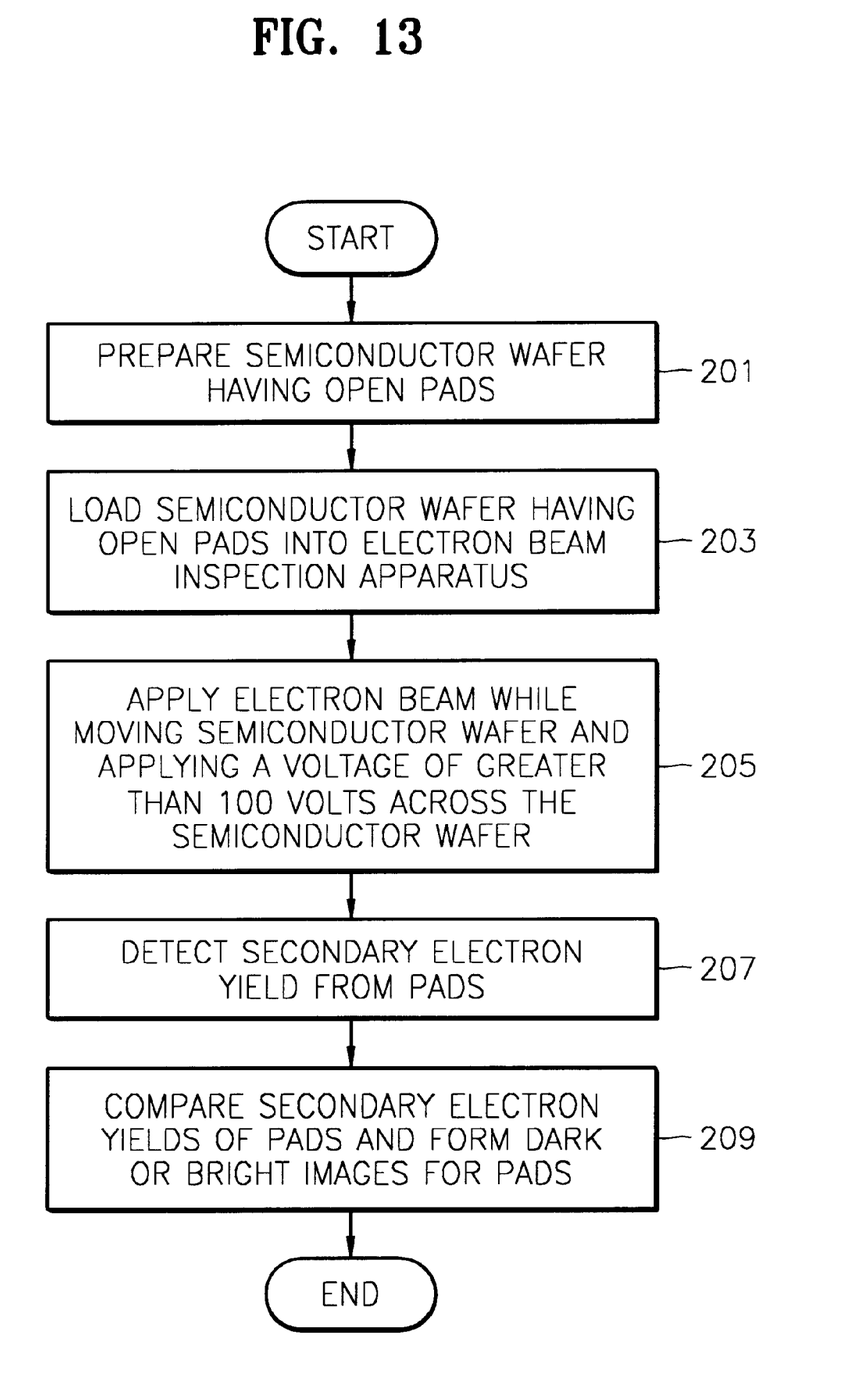
FIG. 13 is a flow diagram of steps that illustrates methods of inspecting integrated circuit substrates according to the present invention.

FIG. 13 is a flowchart of operations illustrating in-line monitoring of the state (open or not-open) of a contact hole. These operations may be performed by testing the semiconductor substrate shown in FIGS. 9 or 11 with the electron beam inspection apparatus shown in FIG. 1. In detail, semiconductor substrates having exposed conductive pads are prepared in-line during fabrication of a semiconductor device (Block 201). The semiconductor substrate having the conductive pads may be formed by depositing conductive layers in-line during fabrication of a semiconductor device, and then performing a chemical mechanical polishing or etch-back process thereon. Subsequently, the semiconductor substrate having the exposed conductive pads is loaded into an electron beam inspection apparatus (Block 203). Next, while the loaded semiconductor substrate is moved in the x and y axes directions, an electron beam is irradiated onto the plurality of conductive pads (Block 205). In this case, the voltage difference between the top and bottom surfaces of the semiconductor substrate can be set in the range of 800–1500 volts, using a high-voltage electron beam apparatus. Otherwise, the voltage difference between the top and bottom surfaces of the semiconductor substrate can be set in the range of 100–800 volts using a low-voltage electron beam inspection apparatus. Then, in the event an unetched material layer 117 or residue is present in a contact hole, as shown in FIG. 10, electrons emitted by the inspection apparatus will be blocked by the residue from moving into the substrate 101. The blocked electrons may accumulate on the surfaces of the conductive pads 115. On the other hand, in the event an unetched material layer 117 or residue is not present in a contact hole, electrons will not accumulate on the surface of the respective conductive pad 115 but will flow into the silicon substrate 101 through the corresponding impurity region 113.

Next, the number of secondary electrons emitted from the plurality of conductive pads using the electron beam inspection apparatus is detected by a secondary electron detector (Block 207). Here, many secondary electrons can be detected as coming from those surfaces of the conductive pads where many electrons are accumulated because of the repulsive forces between the electrons. On the surfaces of the conductive pads where electrons are not accumulated, a relatively small amount of secondary electrons are detected. The amount of secondary electrons detected on two neighboring conductive pads (among the plurality of conductive pads) can then be compared to each other and dark or bright images are formed depending on the difference in secondary electron yields. Using techniques well known to those skilled in the art, the dark and bright images can be used to determine whether a contact hole of the semiconductor substrate is in an open state or a not-open state because an insulating residue is present (Block 209).

Figure 21:
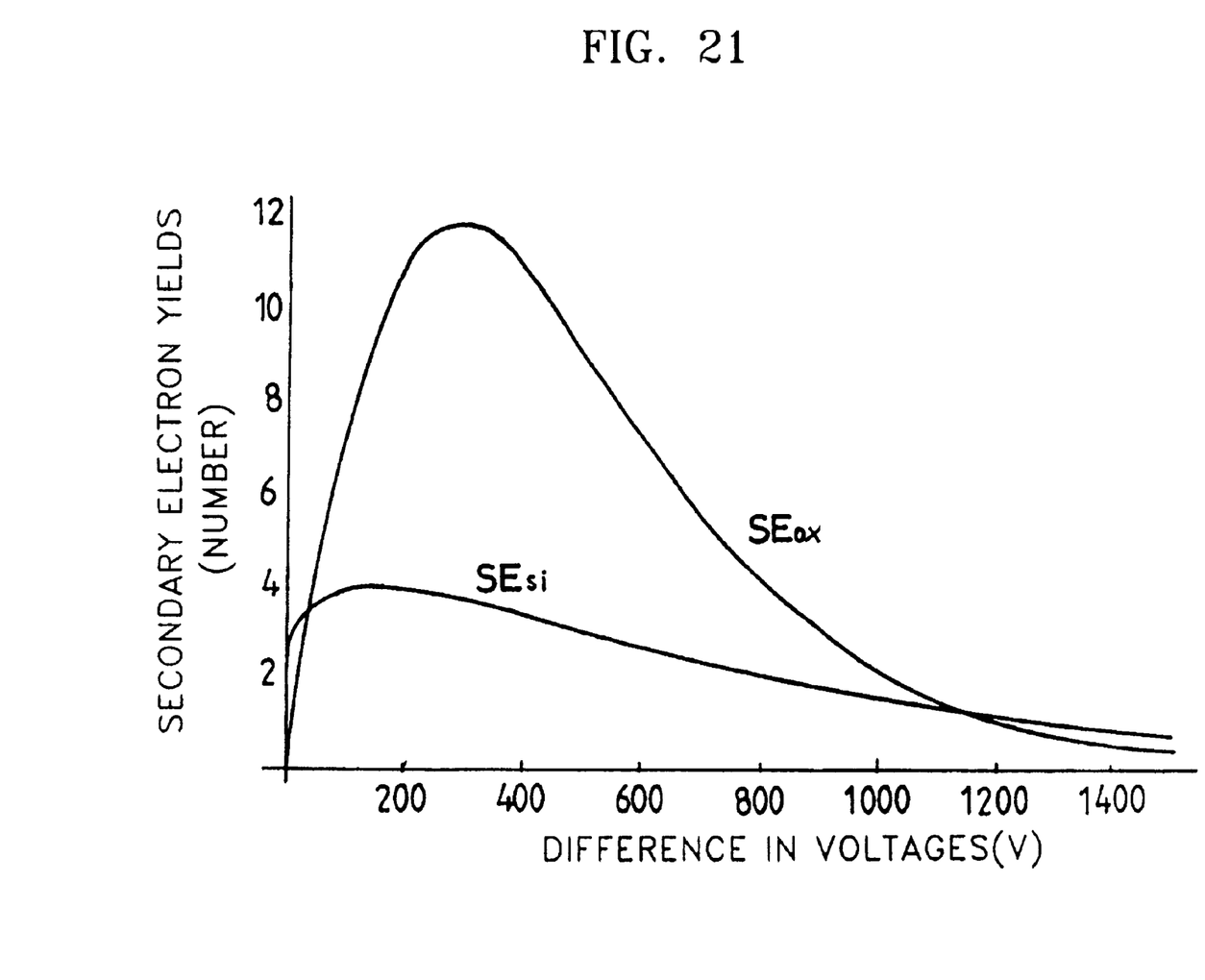
FIG. 21 is a graph of secondary electron yield (y-axis) versus voltage (x-axis) for oxide and silicon.

In the event a high-voltage electron beam inspection apparatus is used, a bright image will be exhibited for those contact holes that contain insulating residues and a dark image will be exhibited for those contact holes that do not contain an insulating residue. However, if a low-voltage electron beam inspection apparatus is used, a dark image will be exhibited for those contact holes that contain insulating residues and a bright image will be exhibited for those contact holes that do not contain an insulating residue. As illustrated best by FIG. 21, this reversal in dark and bright images is a natural consequence of the change in relative electron yields between silicon and silicon dioxide at voltages greater than 800 volts.

Figure 14:
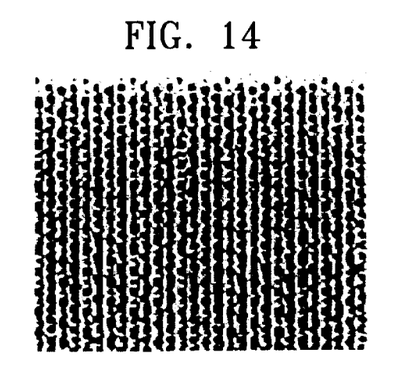
FIG. 14 illustrates images of contact holes observed when a semiconductor substrate having a cross-section as illustrated by FIG. 2 is inspected by the apparatus of FIG. 1 at low voltage.
Figure 15:
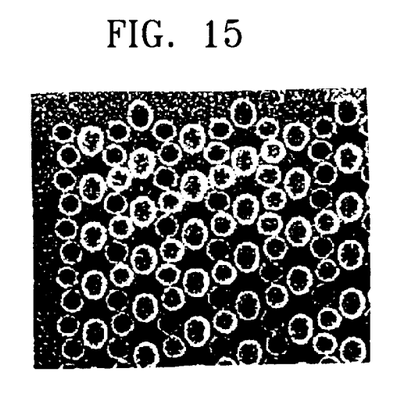
FIG. 15 illustrates images of contact holes observed when a semiconductor substrate having a cross-section as illustrated by FIG. 9 is inspected by the apparatus of FIG. 1 at low voltage.

FIGS. 14 and 15 illustrate images of contact holes observed when the semiconductor substrates shown in FIGS. 2 and 9 are tested with a low-voltage electron beam inspection apparatus. In detail, FIG. 14 illustrates an image of a contact hole in the semiconductor substrate shown in FIG. 2, having undergone a self-aligned contact process prior to formation of conductive plugs. FIG. 15 illustrates an image of contact holes observed when the semiconductor substrate having conductive plugs formed therein as shown in FIGS. 9 or 11. As shown in FIG. 14, when a semiconductor substrate having undergone a self-aligned contact process is tested with a low-voltage electron beam inspection apparatus, bright and dark images of contact holes are not discernable, thereby preventing a determination of whether an insulating residue remains in a contact hole. However, as shown in FIG. 15, when a semiconductor substrate is examined after conductive plugs are formed in the contact holes, bright and dark images of contact holes are discernable, thereby enabling a reliable determination of whether insulating residues remain in the contact holes. In FIG. 15, a dark image represents a not-open state of a contact hole and a bright image represents an open state of a contact hole.

Figure 16:
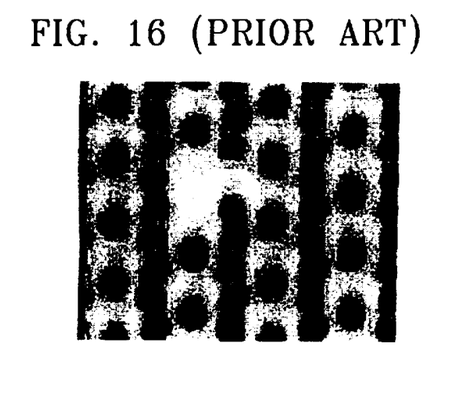
FIG. 16 illustrates images of contact holes observed when a semiconductor substrate having a cross-section as illustrated by FIG. 2 is inspected by the apparatus of FIG. 1 at high voltage.
Figure 17:
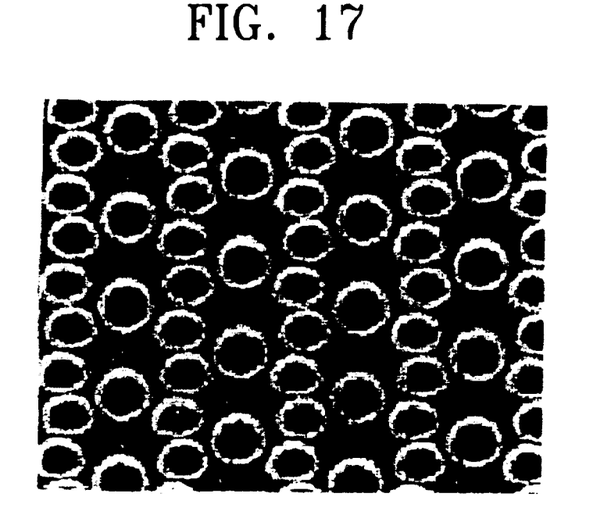
FIG. 17 illustrates images of contact holes observed when a semiconductor substrate having a cross-section as illustrated by FIG. 9 is inspected by the apparatus of FIG. 1 at high voltage.
Figure 18:
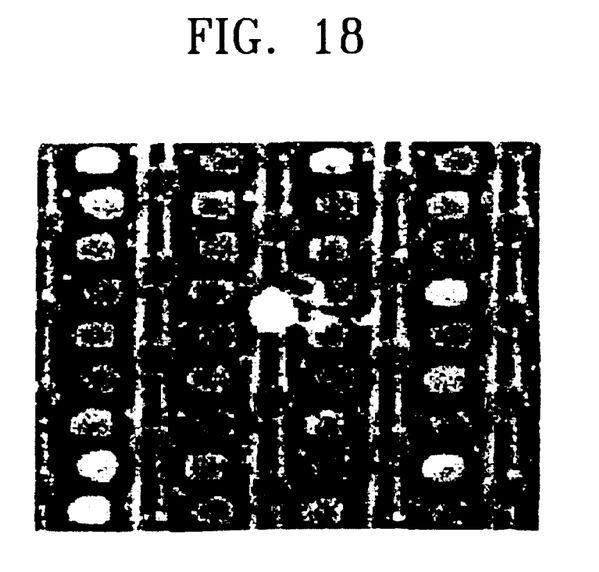
FIG. 18 illustrates images of contact holes observed when a semiconductor substrate having a cross-section as illustrated by FIG. 9 and having being annealed and etched in accordance with the present invention, is inspected by the apparatus of FIG. 1 at high voltage.

FIG. 16 illustrates an image of contact holes observed when the semiconductor substrate shown in FIG. 2 (having undergone a self-aligned contact process) is tested with a high-voltage electron beam inspection apparatus. FIG. 17 illustrates an image of contact holes observed when the semiconductor substrate shown in FIG. 9 (having undergone an annealing process) is tested with a high-voltage electron beam inspection apparatus. FIG. 18 illustrates an image of contact holes observed when the semiconductor substrate shown in FIG. 9, having undergone an annealing process and an etching process, is tested with a high-voltage electron beam inspection apparatus. In detail, FIG. 16 illustrates an image of contact holes in a semiconductor substrate (as shown in FIG. 2) in which the presence of an insulating residue cannot be exactly monitored, as shown in FIGS. 4A–4C, 5A–5C, 6A–6C, 7A–7C and 8A–8C. FIG. 17 illustrates an image of contact holes in a semiconductor substrate observed by a high-voltage electron beam inspection apparatus after forming conductive plugs of polysilicon in the semiconductor substrate (see FIG. 9) and annealing the semiconductor substrate at 850° C. for 2 hours. As shown in FIG. 17, when the image of contact holes is observed by a high-voltage electron beam inspection apparatus after forming the conductive plugs, bright and dark images of the contact hole may not be discernable, thereby possibly preventing a determination of whether a residue is present or not. Nonetheless, FIG. 18 illustrates an image of contact holes in a semiconductor substrate observed by a high-voltage electron beam inspection apparatus after performing annealing on the semiconductor substrate of FIG. 9 and then etching the same using a mixed solution of HF, $NH_4OH$ and pure water. Here, a not-open state of a contact hole can be identified according to whether a bright or dark image is displayed for the contact hole. In FIG. 18, a bright image represents a not-open state of a contact hole (i.e., a residue is present) and a dark image represents an open-state of a contact hole. As described above, if conductive plugs are formed in a contact hole, the state, open or not-open, of the contact hole can be monitored. Also, even if annealing and etching processes are performed after forming the conductive pads, monitoring of whether the contact hole is in an open or not-open state can be achieved.

Figure 19:
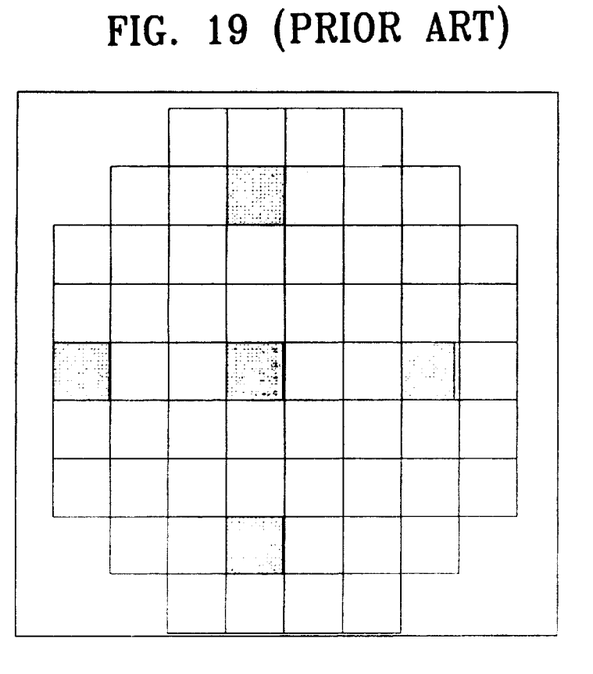
FIG. 19 illustrates a wafer map of the substrate of FIG. 2, observed by a high-voltage electron beam inspection apparatus after a self-aligned contact process has been performed.
Figure 20:
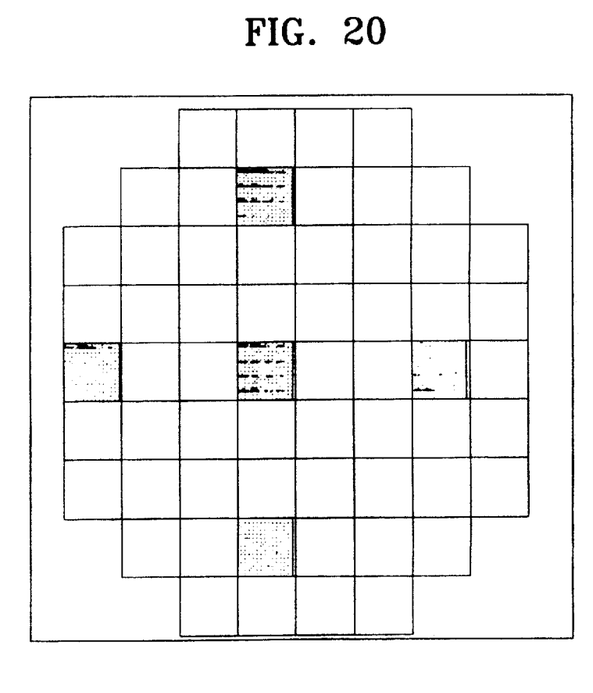
FIG. 20 illustrates a wafer map of the substrate of FIG. 9, observed by a high-voltage electron beam inspection apparatus after a self-aligned contact process and etching process have been performed.

FIG. 19 illustrates a wafer map of the semiconductor substrate shown in FIG. 2, observed by a high-voltage electron beam inspection apparatus after performing a self-aligned contact process, and FIG. 20 illustrates a wafer map of the semiconductor substrate shown in FIG. 9, observed by a high-voltage electron beam inspection apparatus after performing an etching process and a self-aligned contact process on the semiconductor substrate. In detail, as shown in FIG. 19, if an unetched material layer of less than a predetermined thickness is present in the contact hole, a "not-open" state of the contact hole cannot be exactly identified on the semiconductor substrate having undergone a self-aligned contact process. However, as shown in FIG. 20, if the semiconductor substrate is etched using a mixed solution of HF, $NH_4OH$ and pure water and then annealed at 850° C. for 2 hours, the state, open or not-open, of a contact hole can be identified on the wafer map. Considering the above, it is understood that in the case of using a high-voltage electron beam inspection apparatus, if an annealing process is performed after an etching process, the not-open state of the contact hole can be identified.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A method of inspecting an integrated circuit substrate, comprising the steps of:
    directing a beam of electrons into a first conductive plug located within a first contact hole on the integrated circuit substrate; and
    measuring a quantity of electrons emitted from the first conductive plug to determine an absence or presence of an electrically insulating residue in the first contact hole.

2. The method of claim 1, wherein said directing step is preceded by a step of annealing the integrated circuit substrate.

3. The method of claim 2, wherein the integrated circuit substrate comprises an electrically insulating layer; wherein the electrically insulating layer has a plurality of contact holes therein; wherein each of the plurality of contact holes is filled with a respective conductive plug; and wherein said directing step is preceded by a step of etching the electrically insulating layer.

4. The method of claim 3, wherein said etching step comprises exposing the electrically insulating layer and the conductive plugs therein to an etching solution comprising HF and $NH_4OH$; and wherein said annealing step comprises annealing the integrated circuit substrate at a temperature greater than about 800° C. for a duration greater than about 1 hour.

5. The method of claim 4, wherein the integrated circuit substrate comprises a semiconductor wafer; and wherein said step of directing a beam of electrons into a conductive plug is performed simultaneously with a step of applying a voltage of greater than 800 volts across the semiconductor wafer.

6. The method of claim 1, wherein the integrated circuit substrate comprises a semiconductor wafer; and wherein said step of directing a beam of electrons into a conductive plug is performed simultaneously with a step of applying a voltage of greater than 100 volts across the semiconductor wafer.

7. A method of inspecting an integrated circuit substrate having first and second electrically insulating layers stacked thereon, comprising the steps of:
    directing a beam of electrons into a first conductive plug located within a first contact hole in the first electrically insulating layer; and
    measuring a quantity of electrons emitted from the first conductive plug to determine an absence or presence of an electrically insulating residue in the first contact hole or in a second contact hole that extends in the second electrically insulating layer and is aligned underneath the first contact hole.

8. The method of claim 7, wherein the second electrically insulating layer is disposed between the first electrically insulating layer and a surface of the integrated circuit substrate.

9. The method of claim 8, wherein the second contact hole contains a second conductive plug therein; and wherein the second conductive plug ohmically contacts the first conductive plug.

10. The method of claim 9, wherein said directing step is preceded by a step of annealing the integrated circuit substrate.

11. The method of claim 10, wherein said directing step is preceded by a step of etching the first electrically insulating layer.

12. The method of claim 11, wherein said etching step comprises exposing the first electrically insulating layer and the first conductive plug therein to an etching solution comprising HF and $NH_4OH$; and wherein said annealing step comprises annealing the integrated circuit substrate at a temperature greater than about 800° C. for a duration greater than about 1 hour.

13. The method of claim 12, wherein the integrated circuit substrate comprises a semiconductor wafer; and wherein said step of directing a beam of electrons into a first conductive plug is performed simultaneously with a step of applying a voltage of greater than 800 volts across the semiconductor wafer.

14. The method of claim 7, wherein the integrated circuit substrate comprises a semiconductor wafer; and wherein said step of directing a beam of electrons into a first conductive plug is performed simultaneously with a step of applying a voltage of greater than 100 volts across the semiconductor wafer.

15. A method of inspecting an integrated circuit substrate, comprising the steps of:
- directing a first beam of electrons into a first conductive plug located within a first contact hole on the integrated circuit substrate;
- directing a second beam of electrons into a second conductive plug located within a second contact hole on the integrated circuit substrate;
- measuring a first quantity of electrons emitted from the first conductive plug and a second quantity of electrons emitted from the second conductive plug; and
- determining an absence or presence of an electrically insulating residue in the first contact hole by comparing the first quantity of electrons to the second quantity of electrons.

16. The method of claim 15, wherein said step of directing a first beam of electrons is preceded by a step of annealing the integrated circuit substrate.

17. The method of claim 16, wherein the integrated circuit substrate comprises an electrically insulating layer; wherein the electrically insulating layer has a plurality of contact holes therein; wherein each of the plurality of contact holes is filled with a respective conductive plug; and wherein said step of directing a first beam of electrons is preceded by a step of etching the electrically insulating layer.

18. The method of claim 17 wherein said etching step comprises exposing the electrically insulating layer and the conductive plugs therein to an etching solution comprising HF and $NH_4OH$; and wherein said annealing step comprises annealing the integrated circuit substrate at a temperature greater than about 800° C. for a duration greater than about 1 hour.

19. The method of claim 18, wherein the integrated circuit substrate comprises a semiconductor wafer; and wherein said step of directing a first beam of electrons is performed simultaneously with a step of applying a voltage of greater than 800 volts across the semiconductor wafer.

20. The method of claim 15, wherein the integrated circuit substrate comprises a semiconductor wafer; and wherein said step of directing a first beam of electrons is performed simultaneously with a step of applying a voltage of greater than 100 volts across the semiconductor wafer.

* * * * *